US00PP18497P3

(12) United States Plant Patent
Oud

(10) Patent No.: US PP18,497 P3
(45) Date of Patent: Feb. 19, 2008

(54) ***PETUNIA* PLANT NAMED 'PETELRED'**

(50) Latin Name: *Petunia hybrida*
Varietal Denomination: Petelred

(75) Inventor: Johannes Simon Nicolaas Oud, Bovenkarspel (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/449,491

(22) Filed: Jun. 8, 2006

(65) Prior Publication Data

US 2007/0289042 P1 Dec. 13, 2007

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—Louanne Krawczewicz Myers
(74) *Attorney, Agent, or Firm*—Bruce Vrana

(57) ABSTRACT

A new and distinct cultivar of *Petunia* plant named 'Petelred' characterized by its trailing, outwardly spreading and mounded plant habit, freely branching habit, freely flowering habit, single flowers that are rose-burgundy in color, and good garden performance.

1 Drawing Sheet

Latin name of the genus and species of the plant claimed: *Petunia hybrida.*
Varietal denomination: 'Petelred'.

BACKGROUND OF THE NEW PLANT

The present invention relates to a new and distinct cultivar of *Petunia* plant botanically known as *Petunia hybrida* and referred to by the cultivar name 'Petelred.'

The new *Petunia* is the product of a planned breeding program conducted by the inventor in Enkhuizen, Netherlands. The new *Petunia* cultivar is freely flowering with trailing and spreading plant habit and attractive leaf and flower coloration.

The new *Petunia* originated from a cross-pollination made by the inventor in August 2000 of a proprietary selection of *Petunia hybrida* identified as code number 'A 902' not patented, as the female, or seed parent, with a proprietary selection of *Petunia hybrida* identified as code number 'Y 953,' not patented, as the male, or pollen parent. The new *Petunia* was selected as a single plant from the resulting progeny of the cross-pollination in a controlled environment in Enkhuizen, Netherlands in June 2001.

Asexual reproduction of the new cultivar by terminal vegetative cuttings since June 2001, in Enkhuizen, Netherlands has shown that the unique features of this new *Petunia* are stable and reproduced true to type in successive generations.

SUMMARY OF THE INVENTION

Plants of the cultivar 'Petelred' have not been observed under all possible environmental conditions. The phenotype may vary somewhat with variations in environment such as temperature, light intensity and daylength without, however, any variance in genotype.

The following traits have been repeatedly observed and are determined to the unique characteristics of 'Petelred.' These characteristics in combination distinguish 'Petelred' as a new and distinct cultivar.

1. Trailing, outwardly spreading and mounded plant habit
2. Freely branching habit
3. Freely flower habit
4. Single flowers that are rose-burgundy in color
5. Good garden performance In side-by-side comparisons conducted in Enkhuizen, Netherlands, plants of the *Petunia* named 'Petelred' differed from plants of the female parent selection is the following characteristic:

1. Plants of the *Petunia* named 'Petelred' have rose-burgundy flowers whereas flowers of the female parent selection are rose.

In side-by-side comparisons conducted in Enkhuizen, Netherlands, plants of the *Petunia* named 'Petelred' differed from plants of the male parent selection in the following characteristic:

1. Plants of the *Petunia* named 'Petelred' and the male parent selection differed in habit. The plants of the *Petunia* named 'Petelred' are more mounded whereas the plants of the male parent selection are more trailing.

TABLE 1

DIFFERENCES BETWEEN THE NEW CULTIVAR 'PETELRED' AND A SIMILAR CULTIVAR

| | 'Petelred' | 'Sunrovein' (U.S. Plant Pat. No. 16,468) |
|---|---|---|
| Flower | Color more dark/strong | Petal color less dark/strong |
| Earliness | Earlier | Later |
| Plant habit | Slightly mounding | More flat plant habit |

DESCRIPTION OF THE DRAWING

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Petunia.*

DESCRIPTION OF THE NEW CULTIVAR

The observations and measurements describe plants grown in Enkhuizen, The Netherlands, practice circumstances indoor in hanging baskets of diameter 25 cm during the early Spring with day temperatures ranging from 14 to 16° C., night temperatures ranging from 12 to 14° C. Plants used for the photographs and description were about 10 weeks from planting rooted cuttings.

In the following description, color references are made to The Royal Horticultural Society Colour Chart, 1995 Edition, except where general terms of ordinary dictionary significance are used.

The plant:

*Classification.*—Botanical: *Petunia hybrida.*

*Parentage.*—Female parent: Proprietary selection of *Petunia hybrida* identified as code number 'A 902,' not patented. Male parent: Proprietary selection of *Petunia hybrida* identified as code number 'Y 953,' not patented.

Propagation:

*Type cutting.*—Terminal vegetative cuttings.

*Time to initiate roots.*—Summer and winter: About 12 days at 20° C.

*Time to develop roots, summer.*—About 21 days at 20° C.

*Time to develop roots, winter.*—About 28 days at 16° C.

*Root description.*—Fine, fibrous, white in color.

*Rooting habit.*—Freely branching.

Plant description:

*Form.*—Annual flowering plant; indeterminate; initially upright, then trailing and outwardly spreading; uniformly mounded plant form. Freely branching habit; about ten basal branches each with about five to seven lateral branches. Pinching enhances development of lateral branches.

*Usage.*—Appropriate for hanging baskets, window boxes, patio containers, and landscapes applications.

*Plant height.*—About 15 cm.

*Plant diameter* (*area of spread*).—About 55 cm.

*Vigor.*—Vigorous; rapid growth rate.

*Lateral branches.*—Length: About 20 cm. Diameter: About 4.5 mm. Internode length: About 2–3 cm. Texture: Pubescent. Color: 144C.

*Foliage description.*—Arrangement: Alternate before flowering; opposite after flowers develop simple. Length: About 6.5 cm. Width: About 3.7 cm. Shape: Broad elliptic. Apex: Broadly acute. Base: Attenuate. Margin: Entire. Texture, upper and lower surfaces: Sparsely pubescent; glandular. Venation pattern: Pinnate, arcuate.

*Color.*—Developing and fully expanded leaves, upper surface: Between 147A–B. Developing and fully expanded leaves, lower surface: 147B. Venation, upper surface: 143C. Venation, lower surface: 147C. Petiole length: About 10 mm. Petiole diameter: About 3 mm. Petiole color, upper and lower surfaces: 144B. Petiole texture: Sparsely pubescent.

Flower description:

*Flower type and habit.*—Single salverform flowers; flowers face mostly upward and outward; axillary. Freely flowering habit, about two to three open flowers and about three flower buds per lateral branch at a time.

*Natural flowering season.*—Long day responsive; lower flowering period, spring until frost in the autumn; flowering continuous during this period. Plants start flowering about eight weeks after planting rooted cuttings. Flowers persistent.

*Flower longevity on the plant.*—About seven to ten days.

*Fragrance.*—Faint, sweet.

*Flower size.*—Diameter: About 6 cm. Tube length: About 3.5 cm. Flower depth: 0.4 cm. Throat diameter, distal end: About 1.5 cm. Tube diameter, proximal end: About 3 mm.

*Flower buds.*—Length: About 4.2 cm. Diameter: About 8 mm. Shape: Elongated oblong with ruffled apices. Color: Darker than N79A, greyer.

*Petals.*—Quantity/arrangement: About five petals fused in a single whorl, funnel form. Length from throat: About 2.5 cm. Width: About 3 cm. Shape: Roughly fan-shaped. Apex: Retuse. Margin: Slightly dentated. Texture, upper and lower surfaces: Smooth, velvety.

*Color.*—When opening, upper surface: Much deeper than 58A; venation N79A. When opening, lower surface: 64C with lots of veins; venation N77A. Fully opened, upper surface: Much deeper than 58A; venation N79A. Fully opened, lower surface: 64C with lots of veins; venation N77A. Flower throat (inside): N79B. Flower tube (outside): N79B. Venation, throat: N79A. Venation, tube: N77A.

*Sepals.*—Arrangement/appearance: Single whorl of five sepals fused at base, star-shaped. Length: About 1.5 cm. Width: About 7 mm. Shape: Ligulate. Apex: Rounded. Margin: Entire. Texture, upper and lower surfaces: Pubescent. Color, upper surface: 147A. Color, lower surface: 147A.

*Peduncles.*—Length: About 3.3 cm. Width: About 2 mm. Angle: About 45 to 60° from the stem. Strength: Strong. Texture: Pubescent. Color: 144A.

*Reproductive organs.*—Stamens, quantity per flower: About five. Anther shape: Ovoid. Anther size: About 1.5 mm by 2 mm. Anther color: 159B. Pollen amount: Scarce. Pollen color: 159B. Pistils, quantity per flower: One. Pistil length: About 1.9 cm. Style length: About 1.8 cm. Style color: 144D. Stigma shape: Anvil-shaped. Stigma color: N144A. Ovary color: 143A. Seed/fruit: Seed and/or fruit production has not been observed.

Disease and pest resistance: Plants of the *Petunia* named 'Petelred' have not been noted to be resistant to pathogens or pests common to *Petunia.*

Garden performance: Plants of the *Petunia* named 'Petelred' have been observed to have good garden performance. Plants of the *Petunia* named 'Petelred' have been noted to tolerate rain, wind, and temperatures from 0 to 30° C.

What is claimed is:

1. A new and distinct cultivar of *Petunia* plant named 'Petelred', as substantially illustrated and described herein.

* * * * *

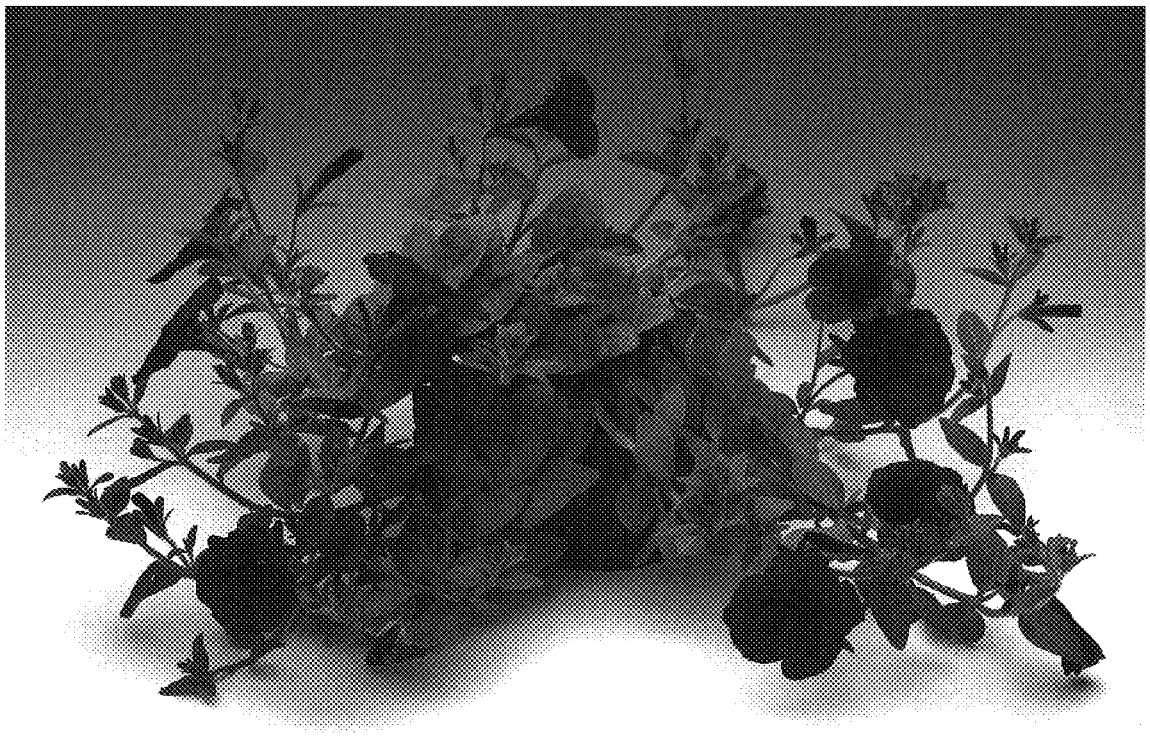

UNITED STATES PATENT AND TRADEMARK OFFICE

CERTIFICATE OF CORRECTION

PATENT NO. : PP 18,497 P3
APPLICATION NO. : 11/449491
DATED : February 19, 2008
INVENTOR(S) : Oud It is certified that error appears in the above-identified patent and that said Letters Patent is hereby corrected as shown below:

At column 3, line 55, under "Foliage description" and after "Arrangement:" insert --;-- following "develop"

At column 4, line 8, after "Natural flowering season" delete "lower" and insert therefor --long--

Signed and Sealed this

Twenty-seventh Day of May, 2008

JON W. DUDAS
*Director of the United States Patent and Trademark Office*